United States Patent
Kilger et al.

(10) Patent No.: US 6,399,304 B1
(45) Date of Patent: Jun. 4, 2002

(54) SEQUENTIAL ACTIVATION OF ONE OR MORE ENZYMATIC ACTIVITIES WITHIN A THERMOCYCLING REACTION FOR SYNTHESIZING DNA MOLECULES

(75) Inventors: Christian Kilger; Michael Motz, both of Heidelberg (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/577,047

(22) Filed: May 24, 2000

Related U.S. Application Data

(63) Continuation-in-part of application No. 09/339,103, filed on Jun. 24, 1999, which is a continuation-in-part of application No. 08/991,184, filed on Dec. 16, 1997, now Pat. No. 6,225,092.

(30) Foreign Application Priority Data

Dec. 20, 1996 (DE) .......................................... 196 53 494

(51) Int. Cl.[7] .............................. C12Q 1/68; C12P 19/34
(52) U.S. Cl. ........................... 435/6; 435/91.9; 435/91.2
(58) Field of Search .......................... 435/6, 91.1, 91.2, 435/810

(56) References Cited

U.S. PATENT DOCUMENTS

| | | | |
|---|---|---|---|
| 4,962,020 A | 10/1990 | Tabor et al. .................... | 435/6 |
| 5,338,671 A | * 8/1994 | Scalice et al. ............. | 435/91.2 |
| 5,409,811 A | 4/1995 | Tabor et al. .................... | 435/6 |
| 5,427,911 A | 6/1995 | Ruano ........................... | 435/6 |
| 5,432,065 A | 7/1995 | Fuller ........................ | 435/91.1 |
| 5,512,462 A | 4/1996 | Cheng ........................ | 435/91.2 |
| 5,556,772 A | 9/1996 | Sorge et al. ............... | 435/91.2 |
| 5,614,365 A | 3/1997 | Tabor et al. .................... | 435/6 |
| 5,677,152 A | * 10/1997 | Birch et al. ................. | 435/91.2 |
| 5,789,168 A | 8/1998 | Leushner et al. .............. | 435/6 |
| 5,830,657 A | 11/1998 | Leushner et al. .............. | 435/6 |
| 5,928,906 A | 7/1999 | Köster et al. .............. | 435/91.2 |

FOREIGN PATENT DOCUMENTS

| | | |
|---|---|---|
| EP | 0 727 496 | 8/1996 |
| EP | 0 771 870 | 5/1997 |

OTHER PUBLICATIONS

Chen et al., Tissue Antigens 51, 645–648 (Jun. 1998).*
Chemical Abstracts, vol. 125, No. 25, 1996, p. 393, 125:319052.
Deng et al., Journal of Microbiological Methods, vol. 17 (1993) 103–113, "Simultaneous amplification and sequencing of genomic DNA (SAS) . . .".
Hwang et al., Analytical Biochemistry, vol. 231, No. 2, Nov. 1995, pp. 460–463, "Direct automated sequencing of singl lambda–phage plaques by exponential amplification sequencing".
International Publication No. WO 97/42348, published Nov. 13, 1997.
International Publication No. WO 97/41257, published Nov. 6, 1997.
International Publication No. WO 97/41258, published Nov. 6, 1997.
International Publication No. WO 97/41259, published Nov. 6, 1997.
International Publication No. WO 97/40939, published Nov. 6, 1997.
International Publication No. WO 97/23650, published Jul. 3, 1997.
International Publication No. WO 96/41014 published Dec. 19, 1996.
International Publication No. WO 96/10640 published Apr. 11, 1996.
International Publication No. WO 94/26766 published Nov. 24, 1994.
International Publication No. WO 93/02212, published Feb. 4, 1993.
Kilger et al., Biol. Chem., vol. 378, pp 99–105, Feb. 1997, "Direct exponential Amplification and Sequencing (DEXAS) of Genomic DNA".
Kilger et al., Nucleic Acids Research, vol. 25, No. 10, May 1997, pp. 2032–2034 "Direct DNA sequence determination from total genomic DNA".
Rao, Analytical Biochemistry, vol. 216, 1–14 (1994), "Direct Sequencing of Polymerase Chain Reaction–Amplified DNA".
Sarkar et al., Nucleic Acids Research, 1995, vol. 23, No. 7, pp 1269–1270, "Semi Exponential cycle sequencing".
Tabor et al., Proc. Natl. Acad. Sci. USA, vol. 92, pp 6339–6343, Jul. 1995, "A single residue in DNA polymerases of the *Escherichia coli* DNA polymerase I family is critical for distinguishing between deoxy–and dideoxyribonucleotides".

* cited by examiner

Primary Examiner—Kenneth R. Horlick
(74) Attorney, Agent, or Firm—Arent Fox Kintner Plotkin & Kahn, PLLC

(57) ABSTRACT

Method for synthesizing or sequencing a nucleic acid molecule in a thermocycling reaction which initially comprises a nucleic acid molecule, a first primer, a second primer, a reaction buffer, a first thermostable enzyme e.g. a DNA polymerase, (optionally) a thermostable pyrophosphatase, deoxynucleotides or derivatives thereof and in case of a sequencing method a dideoxynucleotide or a derivative thereof and which is characterized in that the thermocycling reaction additionally contains a second thermostable enzyme e.g. a DNA polymerase which, in comparison to the said first thermostable enzyme, exhibits a different enzymatic activity as e.g. has a reduced ability to incorporate dideoxynucleotides as well as the use of the said method. At least one polymerase is initially inhibited whereby the inhibiting agent loses inhibitory ability at cycles of the thermocycling reaction. When both polymerases are inhibited, the inhibiting agents should loose their inhibitory ability at different time points of the reaction.

35 Claims, 10 Drawing Sheets

Fig.2A

NON-COMPLEX MIXTURES

| A: SIZE | A: NUMBER OF MOLECULES | A: TOTAL NUMBER OF NUCLEOTIDES | B: SIZE | B: NUMBER OF MOLECULES | B: TOTAL NUMBER OF NUCLEOTIDES | (A:B) RATIO OF NUMBER OF MOLECULES | (A:B) RATIO OF TOTAL NUMBER OF NUCLEOTIDES |
|---|---|---|---|---|---|---|---|
| 1000 bp | $1 \times 10^9$ | $1 \times 10^{12}$ | $3 \times 10^6$ bp | 1000 | $3 \times 10^9$ | $1 \times 10^6$ | 333 |

"A" IS A TARGET DNA MOLECULE IN A PCR PRODUCT.
"B" REPRESENTS BACKGROUND DNA MOLECULES IN THE PCR PRODUCT.

Fig.2B

MEDIUM COMPLEX MIXTURES

| A: SIZE | A: NUMBER OF MOLECULES | A: TOTAL NUMBER OF NUCLEOTIDES | B: SIZE | B: NUMBER OF MOLECULES | B: TOTAL NUMBER OF NUCLEOTIDES | (A:B) RATIO OF NUMBER OF MOLECULES | (A:B) RATIO OF TOTAL NUMBER OF NUCLEOTIDES |
|---|---|---|---|---|---|---|---|
| 1000 bp | 300 | $3 \times 10^5$ | $3 \times 10^6$ bp | 1 | $3 \times 10^6$ | 300 | 0.1 |

"A" IS A TARGET DNA MOLECULE IN THE DNA FROM A COLONY OF BACTERIAL CELLS.
"B" REPRESENTS BACKGROUND DNA MOLECULES IN THE DNA FROM THE COLONY OF BACTERIAL CELLS.

Fig.2C

COMPLEX MIXTURES

| A: SIZE | A: NUMBER OF MOLECULES | A: TOTAL NUMBER OF NUCLEOTIDES | B: SIZE | B: NUMBER OF MOLECULES | B: TOTAL NUMBER OF NUCLEOTIDES | (A:B) RATIO OF NUMBER OF MOLECULES | (A:B) RATIO OF TOTAL NUMBER OF NUCLEOTIDES |
|---|---|---|---|---|---|---|---|
| 1000 bp | 1 | 1000 | $3 \times 10^9$ bp | 1 | $3 \times 10^9$ | 1 | $3 \times 10^{-6}$ |

"A" IS AN ALLELE OR A SINGLE COPY OF A HUMAN GENE AS A TARGET DNA MOLECULE IN A HUMAN GENOMIC DNA.
"B" REPRESENTS BACKGROUND DNA MOLECULES IN THE HUMAN GENOMIC DNA.

ONE PRIMER PAIR

MORE THAN ONE PRIMER PAIR

THE LABELED PRIMER IS FULLY, PARTIALLY OR NOT OVERLAPPING WITH THE UNLABELED PRIMERS WHICH ARE FLANKING PRIMERS TO THE LABELED PRIMER.

TWO PRIMER PAIRS

MORE THAN TWO PRIMER PAIRS OR SPECIAL EMBODIMENTS

LABEL MEANS A LABEL FOR e.g. FLUORESCENT DETECTION OR e.g. A BIOTHIN-LABEL

UNLABELED, MAY ALSO IN A PREFERRED EMBODIMENT BE LABELED IN A COLOR DIFFERENT FROM THE OTHER LABEL

LABEL DISTRIBUTION USING 4 COLOR DETECTION:

THE LABELED PRIMERS ARE FULLY, PARTIALLY OR NOT OVERLAPPING WITH THE UNLABELED PRIMERS WHICH ARE FLANKING PRIMERS TO THE LABELED PRIMERS.

SEQUENTIAL ACTIVATION OF ONE OR MORE ENZYMATIC ACTIVITIES WITHIN A THERMOCYCLING REACTION FOR SYNTHESIZING DNA MOLECULES

CROSS REFERENCE TO RELATED APPLICATION

This application is a continuation-in-part of U.S. application Ser. No. 09/339,103, filed Jun. 24, 1999, which is a continuation-in-part of U.S. patent application Ser. No. 08/991,184, filed Dec. 16, 1997, U.S. Pat. No. 6,225,092, the disclosure of which is herein incorporated by reference.

The present invention relates to a method involving sequential activation of one or more enzymatic activities within a reaction as e.g. sequencing, amplification or uncoupled, direct, exponential amplification and sequencing of DNA molecules, coupled reversed transcription and amplification reactions wherein all these reactions contain at least two different enzyme activities.

Especially, the present invention relates to a method for the uncoupled, direct, exponential amplification and sequencing of DNA molecules in a thermocycling reaction which initially comprises a nucleic acid molecule, a first primer, a second primer, a reaction buffer, deoxynucleotides or derivatives thereof and at least one dideoxynucleotide or another terminating nucleotide wherein the thermocycling reaction contains at least two thermostable DNA polymerases with different properties for incorporating dideoxynucleotides wherein one of the two thermostable DNA polymerases is activated in a later cycle of the thermocycling reaction than the other thermostable DNA polymerase. The present invention further relates to the use of a second primer pair called "silent primers" which comprises a third and eventually a forth primer, which are not labeled or differently labeled, compared to the first primer pair at least one of which is labeled or biotinylated.

The DNA sequence determination as developed by Sanger et al. ((1977) *Proc. Natl. Acad. Sci. USA* 74, 5463–5467) is usually carried out with a T7 DNA polymerase (Tabor S. and Richardson, C. C. (1989) *Proc. Natl. Acad. Sci. USA* 86, 4076–4080). This method requires relatively large amounts of a purified, single-stranded DNA template. Recently cycle sequencing has been developed (Murray, V. (1989) *Nucleic Acids Res.* 17, 8889). This method does not require a single-stranded template and allows the sequence reaction to be initiated with relatively small amounts of template. However, the template DNA has to be purified to almost complete homogeneity and is usually prepared by means of cloning in plasmids (Bolivar, F. et al., (1977) *Gene* 2, 95–113) and subsequent plasmid purification (Birnboim, H. C. and Doly, J. (1979) *Nucleic Acids Res.* 7, 1513–1523) or by means of PCR amplification (Mullis, K. B. and Faloona, F. A. (1987) *Methods Enzymol.* 155, 335–350). Only one primer is used in both of the methods described above.

In one embodiment of cycle sequencing which is referred to as "coupled amplification and sequencing" or "CAS" Ruano and Kidd ((1991) *Proc. Natl. Acad. Sci. USA* 88, 2815–2819; U.S. Pat. No. 5,427,911) have shown that one can use a two-step protocol to generate sequences from DNA templates. In the first step 15 PCR cycles are carried out with Taq DNA polymerase in the absence of dideoxynucleotides in order to prepare an adequate amount of sequencing template. In a second step in which dideoxynucleotides and a labelled primer are added, CAS produces the sequence as well as the additional amplification of the target sequence. Two primers are used in both steps of the method.

Many DNA polymerases, including the Taq DNA polymerase, that are used in coupled DNA sequencing reactions strongly discriminate against ddNTPs and preferably incorporate dNTPs if they are furnished with a mixture of ddNTPs as well as dNTPs. Hence the optimization of the CAS process requires careful titration of the dideoxynucleotides.

Furthermore since coupled amplification and sequencing depends on the amount of the initial DNA, the distance between the two primers and the concentrations and the ratios of the ddNTPs and dNTPs relative to one another, the optimization of coupled amplification and sequencing reactions (CAS) requires that the reaction conditions are individually optimized for a particular DNA fragment.

Other known thermostable polymerases that are used for sequencing, e.g. ThermoSequenase and Taquenase, carry a mutation which is known as the "Tabor Richardson" mutation (Tabor, S. & Richardson, C. C. (1995) *Proc. Natl. Acad. Sci. USA* 92, 6339–6343) in which a tyrosine is present instead of a phenylalanine in the cleft of the enzyme which, during polymerization of the DNA molecule being formed, is responsible for discriminating between the incorporation of either deoxynucleotides or dideoxynucleotides. Such enzymes or functional derivatives thereof have an increased ability to incorporate dideoxynucleotides into DNA fragments that are being formed and can be used to improve the signal uniformity in sequencing reactions. The increased ability of the aforementioned DNA polymerases with a Tabor-Richardson mutation to incorporate dideoxynucleotides increases the statistical probability that a chain termination occurs due to incorporation of a dideoxynucleotide into a DNA molecule being formed.

Therefore it would be expected that the use of a thermostable polymerase which carries a Tabor-Richardson mutation would limit the distance at which the two primers could be placed on the DNA molecule to be sequenced. This in turn restricts the choice of primers that can be used in a given sequencing reaction.

All the methods described above require an interruption between the first step for the exponential amplification of the template DNA and the second step for the synthesis of truncated DNA molecules and they also require the individual optimization of a given DNA fragment which can be tedious and time-consuming and can lead to errors especially when sequencing a large number of different DNA molecules or when processing large amounts of samples in a hospital or laboratory or when sequencing rare samples for forensic or archaeological studies.

For this reason a method for sequencing nucleic acids was developed which simultaneously potentiates the exponential amplification of molecules of complete length and of molecules of shortened length in the reaction which leads to a reduction of the required amount of starting nucleic acid molecules and does not require an interruption of the exponential amplification step and of the sequencing step so that the whole reaction can be carried out more rapidly and with fewer manipulations (EP 0 849 364 and EP 0 854 196).

Methods for sequencing nucleic acid molecules were developed (called DEXAS and DEXTAQ, respectively), which allows an increase in the distance between the positions of the two primers on the nucleic acid molecule to be sequenced (EP 0 849 364 and EP 0 854 196). These methods are relatively independent of the distance between the said primers and in general does not require an optimization of the reaction conditions for each DNA fragment to be sequenced.

DEXAS and DEXTAQ are rapid and reliable methods for sequencing nucleic acid molecules that can be carried out in an uninterrupted manner, in a single step and in a single container. DEXAS and DEXTAQ simultaneously increase the exponential amplification of molecules of complete length as well as of molecules of shortened length which leads to a reduction of the initial amount of nucleic acid molecules that are required for the cycling reaction.

In contrast to the DEXAS method that makes use of one enzyme having reduced discrimination against ddNTPs compared to wild-type Taq DNA polymerase in the buffer or under the conditions that are used for the thermocycling DEXTAQ is carried out by adding two different types of DNA polymerases to the initial cycle sequencing reaction: a first thermostable DNA polymerase and a second thermostable DNA polymerase with a reduced ability to incorporate dideoxynucleotides compared to the said first thermostable DNA polymerase. The first DNA polymerase mainly produces shortened products that accumulate exponentially during the cycles and contribute to the sequence ladder that is generated whereas the second DNA polymerase, which has a reduced ability to incorporate dideoxynucleotides compared to the first said thermostable DNA polymerase, primarily produces products of complete length which accumulate exponentially and serve in subsequent cycles as a template for the production of further DNA strands of complete length as well as templates for extensions which contribute to the sequencing reaction. Hence the combination of the different properties of the two polymerases, i.e. the ability of the first DNA polymerase to efficiently incorporate dideoxynucleotides and the ability of the second DNA polymerase to efficiently incorporate deoxynucleotides, leads to a considerably increased efficiency of the uncoupled, direct, exponential amplification and sequencing reaction.

An object of the present invention is to provide an improved method for sequencing nucleic acid molecules which leads to a further increase in the distance at which both primers can be positioned on the nucleic acid molecule to be sequenced. A further object of the present invention is to provide an improved method for sequencing a nucleic acid which further increases the signal-to-noise ratio of specific, correctly terminated molecules to unspecifically terminated molecules resulting in a more accurate detectable sequence ladder. A further object of the present invention is to provide an application of the method according to the invention for sequence determination in medical diagnostics, forensics and population genetics.

The present invention comprises a method for synthesizing a nucleic acid molecule in a thermocycling reaction which initially comprises a nucleic acid molecule, a first primer (i), a second primer (ii) a reaction buffer, deoxynucleotides or derivatives thereof wherein the thermocycling reaction contains at least two thermostable enzymes with different enzyme activities, whereas at least one enzyme exhibits DNA polymerase activity and wherein one of the two enzymes is activated in a later cycle of the thermocycling reaction than the other thermostable enzyme.

The subject of the present invention is further to provide a method for sequencing a nucleic acid molecule in a thermocycling reaction which initially comprises a nucleic acid molecule, a first primer, a second primer, a reaction buffer, deoxynucleotides or derivatives thereof and at least one dideoxynucleotide or another terminating nucleotide wherein the thermocycling reaction contains at least two thermostable DNA polymerases with different enzyme activities for incorporating dideoxynucleotides wherein one of the two thermostable DNA polymerases is activated in a later cycle of the thermocycling reaction than the other thermostable DNA polymerase. Preferably, the thermocycling reaction contains a first polymerase and a second thermostable DNA polymerase which has a reduced ability to incorporate dideoxynucleotides in comparison to the first thermostable DNA polymerase. In a preferred embodiment of the invention the first thermostable DNA polymerase is activated in a later cycle of the thermocycling reaction than the second thermostable DNA polymerase which has a reduced ability to incorporate dideoxynucleotides in comparison to the first thermostable DNA polymerase. In other words a preferred embodiment of the present invention is a one step method for the uncoupled, direct, exponential and sequential amplification and sequencing of nucleic acid molecules with a first thermostable DNA polymerase that is inhibited in its polymerization function by e.g. a irreversible removable modification or an inhibiting agent and does not discriminate against ddNTPs and with a second DNA polymerase that discriminates against ddNTPs. Therefore, the first polymerase is released in later cycles of the thermocycling reaction or reaches full activity in later cycles than the second DNA polymerase.

Thus, in one embodiment the reaction may also contain an antibody that is able to inhibit one or more of the polymerases present in the reaction. Optionally instead of using an antibody, the polymerase can be inhibited by another polymerase-inhibiting agent (see e.g. EP 0771 870 A1, the disclosure of which is incorporated by reference).

The most preferred embodiment of the present invention is the above described method for sequencing a nucleic acid molecule whereas both polymerases are initially inhibited by inhibiting agents or by chemical modifications and can be activated in later cycles of the thermocycling reaction wherein one of the polymerases is activated in a later cycle than the other. Further, preferred is the inventive method for sequencing a nucleic acid molecule wherein the first thermostable DNA polymerase is activated in a later cycle of the thermocycling reaction than the second thermostable DNA polymerase which has a reduced ability to incorporate dideoxynucleotides in comparison to the first thermostable DNA polymerase. In this context another especially preferred embodiment of this invention is the use of an antibody against a polymerase and an polymerase-inhibiting agent. For instance, the second polymerase, which discriminates against ddNTP's, is inhibited by an antibody against the second polymerase, whereas the first polymerase is inhibited by another polymerase-inhibiting agent. Examples of another polymerase-inhibiting agent are dicarboxylic acid anhydrides, the chemical modification reagent is an aldehyde, preferably formaldehyde (EP 0 962 526). This would result in a release of the second polymerase at higher temperatures in early cycles of the reaction whereas the first polymerase is released only in later cycles of the reaction.

Polymerase-inhibiting agents, which inhibit by reversible blocking of lysine residues by chemical modification of the .epsilon.-amino group of the lysine residues in the active region of the protein, lead to a reversible inactivation of the protein. Additionally, modification of lysines outside the active region may contribute to the inactivation of the protein through steric interaction or conformational changes. A number of compounds have been described in the literature which react with amino groups in a reversible manner. For example, amino groups have been reversibly modified by trifluoracetylation (see Goldberger and Anfinsen, 1962, Biochemistry 1:410), amidination (see Hunter and Ludwig, 1962, J. Amer. Chem. Soc. 84:3491), maleylation (see Butler et al., 1967, Biochem. J. 103:78), acetoacetylation (see Marzotto et al., 1967, Biochem. Biophys. Res. Commun. 26:517; and Marzotto et al., 1968, Biochim. Biophys. Acta 154:450), tetrafluorosuccinylation (see Braunitzer et al., 1968, Hoppe-Seyler's Z. Physiol. Chem. 349:265), and citraconylation (see Dixon and Perham, 1968, Biochem. J. 109:312–314; and Habeeb and Atassi, 1970, Biochemistry 9(25):4939–4944.

Preferred reagents for the chemical modification of the .epsilon.-amino group of lysine residues are dicarboxylic acid anhydrides, of the general formula

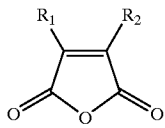

where R1 and R2 are hydrogen or organic radicals, which may be linked, or of the general formula:

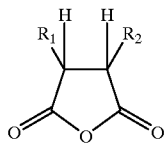

where R1 and R2 are organic radicals, which may be linked, and the hydrogen are cis. The organic radical may be directly attached to the ring by a carbon-carbon bond or through a carbon-hereoatom bond, such as a carbon-oxygen, carbon-nitrogen, or carbon-sulphur bond. The organic radicals may also be linked to each other to form a ring structure as in, for example, 3,4,5,6-tetrahydrophthalic anhydride.

Examples of the preferred reagents include maleic anhydride; substituted maleic anhydrides such as citraconic anhydride, cis-aconitic anhydride, and 2,3-dimethylmaleic anhydride; exo-cis-3,6-endoxo-.DELTA.@4-tetrahydropthalic anhydride; and 3,4,5,6-tetrahydrophthalic anhydride. The reagents are commercially available from, for example, Aldrich Chemical Co. (Milwaukee, Wis.), Sigma Chemical Co. (St. Louis, Mo.), or Spectrum Chemical Mfg. Corp (Gardena, Calif.). Modifications of thermostable DNA polymerases using the substituted maleic anhydride reagents citraconic anhydride and cis-aconitic anhydride are described in the Examples.

The relative stabilities of the amino groups acylated using the above reagents decreases in the following order: maleic anhydride; exo-cis-3,6-endoxo-.DELTA.@4-tetrahydropthalic anhydride; citraconic anhydride; 3,4,5,6-tetrahydrophthalic anhydride; cis-aconitic anhydride; and 2,3-dimethylmaleic anhydride (see Palacian et al., supra).

The methods of the present invention are not limited to the exemplified modifier compounds or to the modification of the protein by chemical modification of lysine residues. Any of the compounds described in the literature which react with proteins to cause the reversible loss of all, or nearly all, of the enzyme activity, wherein the modification is reversible by incubation at an elevated temperature in the amplification reaction buffer, is suitable for preparation of a reversibly inactivated enzyme. As new compounds which reversibly modify proteins become available, these too will be suitable for use in the present methods. Thus, compounds for the preparation of the modified thermostable enzymes of the present invention include compounds which satisfy the following properties:

(1) reaction with a thermostable enzyme which catalyzes primer extension results in a significant inactivation of the enzyme;

(2) incubation of the resulting modified enzyme in an aqueous buffer at about pH 8–9 at a temperature at or below about room temperature (25° C.) results in no significant increase in enzyme activity in less than about 20 minutes; and (3) incubation of the resulting modified thermostable enzyme in an amplification reaction buffer, formulated to about pH 8–9 at room temperature, at an elevated temperature greater than about 50° C. results in at least a two-fold increase in enzyme activity in less than about 20 minutes.

According to this preferred method the first DNA polymerase is inhibited by a polymerase-inhibiting agent and can be released thereof after a certain number of cycles to regain its polymerization activity and mainly produces shortened products that accumulate exponentially during the cycles and thus contribute to the sequencing ladder that is generated. The polymerization-inhibiting agent reversibly loses inhibitory activity at a defined temperature and at a defined time point during the cycle sequencing reaction. Until the first DNA polymerase is released from its inhibitory agent the second DNA polymerase, which has a reduced ability to incorporate dideoxynucleotides compared to the first thermostable DNA polymerase, produces products of complete length of the nucleic acid molecules. That means the second polymerase is active in cycles before the first polymerase will be released. Products of complete length of the nucleic acid molecules accumulate exponentially and serve in subsequent cycles as template for the production of further DNA strands of complete length as well as templates for extensions, which contribute to the sequencing reaction, which starts after the polymerization-inhibiting agent is released from the first thermostable DNA polymerase. The combination of the two different properties of the two polymerases, i.e. the ability of the first DNA polymerase ("1") to efficiently incorporate dideoxynudeotides and the ability of the second DNA polymerase ("2") to efficiently incorporate deoxynudeotides together with the separation of the amplification and sequencing processes from the beginning of the cycling reaction up to a defined number of cycles, at which the polymerase-inhibiting agent of the first polymerase looses its ability to inhibit the polymerization activity of the first polymerase, leads to a considerably increased efficiency of the uncoupled, direct, exponential and sequential amplification and sequencing reaction. Both the full length product as well as the sequencing ladder signals show a marked increase in signal strength, which is correlated with the number of labeled molecules produced by the first polymerase and the number of labeled molecules is correlated with the number of template molecules, which is increased by the separation of the amplification and the sequencing step in this sequential DEXTAQ reaction. Therefore the sequential DEXTAQ method provides a method for nucleic acid sequencing, which can take into account the amount of starting DNA by defining how many cycles of mere amplification are performed before the sequencing reaction starts (see FIG. 1).

The first thermostable DNA polymerase preferably has a reduced discrimination against ddNTPs compared to wild-type Taq DNA polymerase in the buffer or under the conditions that are used for the thermocycling. In a preferred embodiment said first thermostable polymerase is a DNA Taq polymerase (-exo5'-3')(F667Y) or a functional derivative thereof.

In another preferred embodiment the second thermostable DNA polymerase is Taq polymerase or a functional derivative thereof. Polymerases which can be used for the sequential hot-start method are described in the following:

The use of a DNA polymerase (DNA polymerase "1") is preferred as the thermostable first DNA polymerase which, in contrast to wild type Taq DNA polymerase, has a reduced discrimination against ddNTPs in the buffer and under the conditions that are used for the thermocycling and is inhibited by a polymerase-inhibiting agent (e.g. a polymerase-inhibiting agent disclosed in EP 0 771 870 A1, the disclosure of which is incorporated by reference). The polymerase-inhibiting agent loses inhibitory activity by incubating the reaction mixture at an elevated temperature as part of the amplification reaction or during the sequencing reaction. More preferably a DNA polymerase is used which carries a "Tabor-Richardson" mutation (F667Y) or a functional derivative thereof which also has no 5'-3' exonuclease activity such as e.g. Amplitaq FS™ (Taq DNA polymerase (-exo5'-3') (F667), Tabor, S. & Richardson, C. C. (1995) Proc. Natl. Acad. Sci. USA 92, 6339–6343, Taquenase™ (Taq DNA polymerase (272 (-exo5'-3') (F667), Tabor and Richardson (1995),loc. cit.) as well as mixtures thereof or other DNA polymerases and mixtures thereof which are thermostable can also be used in the method of the present invention. The use of Thermosequenase or some other DNA polymerase which has a better ability to incorporate ddNTPs is particularly preferred for the method of the present invention. The use of a DNA polymerase (DNA polymerase "2") is preferred as the thermostable second DNA polymerase, which discriminates against ddNTPs in the buffer and under the conditions that are used for the thermocycling. More preferably a DNA polymerase is used thereof, which also has no 5'-3'exonulease activity such as e.g. Taq DNA polymerase (-exo5'-3'). In a preferred embodiment a DNA polymerase is used, which is inhibited by an antibody such as e.g. PlatinumTaq™ (Life Technologies™, Rockville, Md., USA) as well as mixtures thereof or other DNA polymerases and mixtures thereof, which are thermostable and inhibited by an antibody, can also be used in the method of the present invention.

A DNA polymerase which carries no "Tabor-Richardson" mutation such as e.g. Taq DNA polymerase, Tth DNA polymerase, Klentaq (Taq DNA polymerase) (-exo5'-3'), (Korolev et al. (1995) Proc. Natl. Acad. Sci. USA 92, 9246–9268, W. Barnes in Proc. Natl., Acad. Sci. USA 91 (1994), 2216–2220 and U.S. Pat. No. 5,436,149 is preferably used as the thermostable second DNA polymerase which has a reduced ability to incorporate dideoxynucleotides compared to the first thermostable DNA polymerase. The use of Taq DNA polymerase in the method of the present invention is particularly preferred.

The present invention also enables three or more DNA polymerases to be used in this method.

The concept of the present invention is useful for any temperature-cycled reaction containing at least two enzyme activities e.g. amplification and labeling reactions, reverse transcription, sequencing reactions, ligation reactions, topological manipulation reactions (such as isomerization by topoisomerases or separation of the strands of a DNA double helix by helicases) and restriction reactions; and amplification and restriction enzyme/digestion/ligation. The concept of the present invention is thus the sequential activation of one or more enzymatic activities within a reaction undergoing temperature cycles. Sequential activation means that one of the enzymes reaches full activity only in later cycles in comparison to other enzymes which reaches full activity in earlier cycles of the reaction undergoing temperature cycles. Depending on the application for which the enzymes are used the enzymes may exhibit different properties, e.g. whereas one or more of the polymerases is 5'-3'-exo-deficient or 3'-5'-exo-deficient or have enhanced exo-activities.

Processive polymerases are preferably used for the method according to the invention i.e. the polymerase with a reduced discrimination against ddNTPs preferably has a higher processivity than ThermoSequenase and the polymerase which discriminates against ddNTPs preferably has a higher processivity than the wild-type Taq DNA polymerase. Polymerases according to the invention are most preferably used for the present method whose processivity is higher than that of the wild-type Taq DNA polymerase. Hence it would for example be advantageous to use two polymerases of which processivity is the same as that of T7 polymerase (gene 5 product) when combined with thioredoxin.

In a further preferred embodiment of the method of the invention the ratio of the said primers is 1:1 and alternatively thereto higher than 1:1, e.g., about 2:1 and about 3:1 and most preferably 2:1. The thermocycling reaction of the present invention comprises a first primer and a second primer which serve to simultaneously produce sufficient template molecules of complete length as well as molecules of shortened length which contribute to the sequencing of the nucleic acid molecule. Either one primer is labeled and the other is not or both are differently labeled. In addition each reaction initially contains the nucleic acid template to be sequenced as well as a buffer solution and the four deoxynucleotides or derivatives thereof and one dideoxynucleotide or another terminating nucleotide e.g. 3'-aminonucleotides or 3'-ester- derivatized nucleotides. A thermostable pyrophosphatase can be optionally added. Four reaction mixtures are prepared one for the determination of each base. The present method also comprises the use of labeled terminating nucleotides instead of labeled primers. In the latter case at least one of the primers has to be bound to a solid phase during and/or after the reaction so as to separate complementary strands. Measures as how to bind a primer to a solid phase are known in the art.

In a further preferred embodiment of the method of the invention the said primers have a length that can prevent annealing to unspecific DNA fragments by a high temperature during the cycling. This leads to a good signal-to-noise ratio. The said primers preferably have a length of at least 18 nucleotides.

Primers can be synthesized by means of methods known in the state of the art. For example primers can be synthesized using known methods which do not significantly change the stability or function of the said primers during the nucleic acid sequencing method of the present invention.

Furthermore PNA-DNA hybrid oligonucleotides (see Finn, P. J. et al., N. A. R. 24,3357–3363 (1996), Koch, T. et al., Tetrahedron Letters, 36, 6933–6936 (1995), Stetsenko, D. A, et al., Tetrahedron Letters 37, 3571–3574 (1996), Bergmann, F. et al., Tetrahedron Letters 36, 6823–6826 (1995) and Will, D. W. et al., Tetrahedron 51, 12069–12082 (1995)) are also regarded as primers for the method according to the invention.

In a further preferred embodiment of the method of the invention the said first primer is labelled. Moreover it is preferable that the said first primer and second primer are labelled differently. Any agents or methods known in the state of the art can be used as single or differential labelling agents and methods, provided that the stability or function of the said primer in the DNA sequencing method of the present invention is not significantly changed. For example single and differential labels can be selected from the group which comprises those enzymes such as -galactosidase, alkaline phosphatase, peroxidase and enzyme substrates, coenzymes, dyes, chromophores, fluorescent, chemiluminescent and bioluminescent labels such as FITC, Cy5, Cy5.5, Cy7, Texas-red and IRD40 (Chen et al., (1993), J. Chromatog. A 652: 355–360 and Kambara et al. (1992), Electrophoresis 13: 542–546) ligands or haptens such as e.g. biotin, Big dyes as JOE, TAMRA, 5-FAM, ROX (Heiner et al. (1998) genome Res. 18(5): 557–61) and radioactive isotopes such as $^3H$, $^{35}S$, $^{32}P$, $^{125}I$ and $^{14}C$.

The inventive method is relatively insensitive to various buffers and various deoxynucleotides and dideoxynucleotide concentrations.

The number of thermocycles can be from about 18 to about 50 cycles depending on the amount of template DNA and its purity.

Buffer components which can be used can include Tris-HCl at a pH of about 7.5 to 9.5 and at a concentration of about 50 to 500 mM, preferably of about 100 to 250 mM, $MgCl_2$ at a concentration of about 2 to 6 mM, DMSO at a concentration of about 1 to 5% of the reaction volume, M, Betaine at a concentration of about 0.3 mM, optionally about 0.05 mM 1% mercaptoethanol, about 0,28% Tween20 and/or about 0.02% Nonidet40. Buffer components, however, are not limited to these.

The deacylation of the modified amino groups results from both the increase in temperature and a concomitant decrease in pH. Amplification reactions typically are carried out in a Tris-HCl buffer formulated to a pH of 7.5 to 9.0 at room temperature. At room temperature, the alkaline reaction buffer conditions favor the acylated form of the amino group. Although the pH of the reaction buffer is adjusted to a pH of 7.5 to 9.0 at room temperature, the pH of a Tris-HCl reaction buffer decreases with increasing temperature. Thus, the pH of the reaction buffer is decreased at the elevated temperatures at which the amplification is carried out and, in particular, at which the activating incubation is carried out. The decrease in pH of the reaction buffer favors deacylation of the amino groups.

The change in pH which occurs resulting from the high temperature reaction conditions depends on the buffer used. The temperature dependence of pH various buffers used in biological reactions is reported in Good et al., 1966, Biochemistry 5(2):467–477. For Tris buffers, the change in pKa, i.e., the pH at the midpoint of the buffering range, is related to the temperature as follows: $.DELTA.pKa/°C.=-0.031$. For example Tris-HCl buffer assembled at 25° C. undergoes a drop in pKa of 2.17 when raised to 95° C. for the activating incubation.

Although amplification reactions are typically carried out in a Tris-HCl buffer, amplification reactions may be carried out in buffers which exhibit a smaller or greater change of pH with temperature. Depending on the buffer used, a more or less stable modified enzyme may be desirable. For example, using a modifying reagent which results in a less stable modified enzyme allows for recovery of sufficient enzyme activity under smaller changes of buffer pH. An empirical comparison of the relative stabilities of enzymes modified with various reagents, as provided above, guides selection of a modified enzyme suitable for use in particular buffers.

In an especially preferred embodiment of this invention, agents are added to the reaction mixture which lower the melting point of the DNA, such agents can be, for example, glycerine, trehalose and other such agents as betaine or DMSO known to a person skilled in the art. Alternatively, two different modifying agents can be used which results in the release of the second polymerase in an earlier cycle than the release of the first polymerase. The same may be achieved using two different types of antibodies.

Deoxynucleotides may be selected from, but not limited to, dGTP, dATP, dTTP and dCTP. However, according to the invention, it is also possible to use derivatives of deoxynucleotides. Deoxynucleotide derivatives are defined as those deoxynucleotides or modified deoxynucleotides which are able to be incorporated by a thermostable DNA polymerase into growing DNA molecules that are synthesized in a thermocycling reaction. Examples of deoxynucleotide derivatives include thionudeotides, 7-deaza-2'-dGTP, 7-deaza-2'-dATP, as well as deoxyinosine triphosphate, that can also be used as a substitute deoxynucleotide for dATP, dGTP, dTTP or dCTP. However, deoxynucleotide derivatives are not limited to these examples. The aforementioned deoxynucleotides and derivatives thereof are preferably used at a concentration of about 100 $\mu$M to about 4 mM.

Dideoxynucleotides include, but are not limited to, ddGTP, ddATP, ddTTP and ddCTP. According to the invention, it is also possible to use derivatives of dideoxynucleotides which are defined as those dideoxynucleotides that are able to be incorporated by a thermostable DNA polymerase into growing DNA molecules that are synthesized in a thermocycling reaction. Preferred concentrations of ddNTPs are between about 100 nM and about 100 $\mu$M.

The preferred ratio of dNTPs to ddNTPs (dNTPs:ddNTPs) that is used in the method according to the invention is between about 50:1 and about 1000:1 more preferably between about 1:100– 1:600, especially preferred 1:100–1:400 (in cases where the terminating nucleotides, i.e. ddNTPs are unlabeled).

In a preferred embodiment, the said method is carried out at a temperature at which the signal-to-noise ration of the specific, shortened DNA molecules compared to the unspecific DNA molecules is large enough not to substantially impede reading of the sequence. In the case of human single-copy DNA sequences the highest possible annealing temperature drastically reduces the background.

A typical "Sequential DEXTAQ" reaction temperature cycling profile for detecting the nucleotide sequence of a DNA template molecule consists of three steps, the first step provides 12 to 20 cycles of denaturation, annealing and chain elongation followed by a denaturation step for releasing the inhibited enzyme followed by more 20 to 40 cycles of denaturation, annealing and elongation. The first step in the first part of the cycling profile consists of heat denaturation of the double-stranded target nucleic acid. The exact conditions required for denaturation of the sample nucleic acid depend on the length and composition of the sample nucleic acid. Typically, an incubation at 90° C.–100° C. for about 10 seconds up to about 1 minute is effective to denature the sample nucleic acid. The annealing temperature used in a "Sequential DEXTAQ" reaction typically is about 50° C.–75° C., usually ranging from about 55° C. to 65° C. and maintained for a period of time ranging from about 15 to 45 seconds. Following annealing of primer to template DNA, the reaction mixture will be subjected to conditions sufficient to provide for polymerization of nucleotides to the primer ends. To achieve polymerization conditions, the temperature of the reaction mixture will typically be maintained at a temperature ranging from about 65° C. to 75° C., more preferably at 68° C. to 72° C. for a period of time ranging from about 15 sec to 2 min, usually at 30 sec to 1 min depending on the length of the template DNA. However, depending on the length and temperature of the initial cycling steps, and on the modifier used to inactivate the DNA polymerase, recovery of the DNA polymerase activity of the DNA polymerase, which does discriminate against the ddNTPs and is also modified by a chemical modifier, is not taking place during the first 10 to 20 cycles of the "Sequential DEXTAQ" reaction, more preferably not until cycle 12–15. The maximal recovery of enzyme activity is achieved in the second part of the temperature profile by an extra reaction incubation at about 90° C.–100° C. for 5 to 15 minutes depending on the modifier agent used, more preferably at 95° C. for 10 minutes. This additional incubation step is followed in the third part of the cycling profile by 20 to 40 steps, usually 30 to 35 steps, comprising of denaturation, annealing, where the annealing temperature is the same or differing from the initial cycles depending on the primers used to generate the DNA fragments, which will be detected as the sequencing signals and the polymerization step.

In a further preferred embodiment of the method of the invention, the nucleic acid molecule to be sequenced can be present as total genomic DNA which is in an uncloned or unpurified state. Sequential DEXTAQ functions with about 60 ng total genomic DNA, but also functions with smaller amounts of DNA if multicopy fragments are analysed. Other forms of DNA that can be used as templates include purified, partially purified or unpurified cloned DNA such as e.g. unpurified plasmid DNA from bacterial colonies or cloned or uncloned mitochondrial DNA etc. Furthermore the method of the present invention is relatively independent of the base composition of the template.

In a preferred embodiment the method according to the invention is furthermore characterized in that each thermocycling reaction for the determination of the position of A, G, C and T in the said DNA molecule is carried out in a single step, in a single container, vessel or tube.

In an especially preferred embodiment of the invention the thermocycling reaction additionally contains a thermostable pyrophosphatase.

Since, in addition, all reagents that are necessary for the exponential amplification of fragments of complete length as well as of shortened fragments are present in the initial reaction mixture, the method of the present invention achieves the simultaneous, exponential production of a sequencing template and of a sequence ladder in a single tube without the necessity of interrupting the thermocycling reaction. This means that using the method of the present invention it is possible to determine the nucleic acid sequence in a single step.

The present invention provides a very sensitive method which enables the simultaneous amplification and sequencing of a nucleic acid fragment to be sequenced from a Complex Mixture of nucleic acids, such as total genomic human DNA, without prior amplification of the nucleic acid to be sequenced by means of known methods, in a single step i.e. without interrupting the reaction and indeed such that an unequivocal sequence ladder is readable. The sequential time-released method according to the present invention is an extraordinary improvement over the "normal" DEXTAQ method as described in EP 0 854 196.

The method of the invention can be used for the direct sequencing of nucleic acid molecules in a Complex Mixture. Complex Mixtures are nucleic acid mixtures in which no enriching purification for the target nucleic acid molecule has been performed. However, the nucleic acid may have been isolated from its original source, e.g. cells. In Complex Mixtures, the ratio of the total number of nucleotides in the target nucleic acid molecule and in the background nucleic acid molecules is substantially smaller than one and the ratio of the number of the target nucleic acid molecule to the number of the background nucleic acid molecules is not greatly larger than one, or even smaller than one, and possibly even substantially smaller than one. For instance, the ratio of the number of the target nucleic acid molecule to the number of the background nucleic acid molecules can range from about 0.0001 to about 1. Such Complex Mixtures can be a whole human genomic DNA containing a single copy of a human gene (e.g. p53-gene) as the target DNA molecule for direct sequencing by the method of the invention. FIG. 2c shows an example of the Complex Mixture.

The method according to the invention can also be used for the direct sequencing of nucleic acid molecules in a Medium Complex Mixture. Medium Complex Mixtures are nucleic acid mixtures in which no enriching purification for the target nucleic acid molecule has been preformed. However, the nucleic acid may or may not have been isolated from its original source, e.g. bacterial cells. In Medium Complex Mixtures, the ratio of the total numbers of nucleotides in the target nucleic acid molecule and in the background nucleic acid molecules is close to or smaller than one and the ratio of the number of the target nucleic acid molecule to the number of the background nucleic acid molecules is larger than one. For instance, the ratio of the number of the target nucleic acid molecule to the number of the background nucleic acid molecules can range from about 1 to about 1,000. Such Medium Complex Mixtures can be DNA from a bacterial colony (containing plasmid DNA as the target DNA molecule), DNA from phage plaques (containing M 13 DNA as the target DNA molecule), or partially purified or unpurified mitochondrial DNA. FIG. 2b shows an example of the Medium Complex Mixture.

The method according to the invention can also be used for the direct sequencing of template nucleic acid molecule in a Non-Complex Mixture. Non-Complex Mixtures are nucleic acid mixtures in which the template nucleic acid has been amplified and/or purified or partially purified. The amplification and purification methods can be cloning with subsequent plasmid purification, gradient centrifugation and purification, or the product of PCR in which the PCR product may or may not be purified (the number of PCR cycles in the absence of terminating nucleotides may range from 1 to 50). In Non-Complex Mixtures, the ratio of the number of the target nucleic acid molecule and the number of background nucleic acid molecules is much larger than one. For instance, the ratio of the number of the target nucleic acid molecule to the number of the background nucleic acid molecules can range from about 1,000 to about $1 \times 10^{18}$. FIG. 2a shows an example of the Non-Complex Mixture.

In a further preferred embodiment of the method of the invention the nucleic acid molecule to be sequenced can be present as RNA. A mixture of two polymerases is used: a first DNA polymerase according to the invention e.g. one which contains a "Tabor-Richardson" mutation or a functional derivative thereof (in more general: a DNA polymerase which is able to incorporate terminating nucleotides), such as ThermoSequenase and a second DNA polymerase that is able to reversely transcribe RNA into DNA and has the ability to act as a PCR enzyme. Any thermostable DNA polymerase which has reverse transcriptase activity can be used as a second DNA polymerase for the method of the invention in which RNA is used as the template. Taq DNA polymerase (Jones et al., Nucl. Acids Res. 17:8387–8388 (1989)) or Tth DNA polymerase (Myers et al., Biochemistry 30:7666–7672 (1991)) is preferably used and more preferably Tth DNA polymerase. Tth polymerase reversely transcribes the RNA template into DNA which can then be used by both enzymes: Tth polymerase will primarily generate products of complete length which can serve as templates and ThermoSequenase will produce shortened products (ddNTP incorporation) and thus a sequence ladder.

Suitable buffers include those that are described in Myers et al. (1991) Biochemistry 30: 7666–7672. The following buffer can be used in order to guarantee reverse transcriptase-activity, which will be added as a third enzyme or added by replacing one polymerase, preferably the one discriminating against ddNPTs, with one discriminating against ddNTP's and having a reverse transcriptase activity, to a "Sequential DEXTAQ" reaction:

10 to 500 mM Tris-HCl (pH7.5 to 9.0), 10 to 100 mM KCl, about 1 mM $MnCl_2$ and a $MgCl_2$ concentration of about 2 mM to 6 mM.

In a preferred embodiment of the invention, a DNA polymerase from Carboxydothermus hydrogenoformans is used to sequence RNA. This enzyme disclosed in EP 0 834 569 has reverse transcriptase activity in the presence of Mg ions without the presence of Mn ions. In one of the embodiments of the invention, the polymerase is mutated as described in Tabor and Richardson (Tabor, S. & Richardson, C. C. (1995) *Proc. Natl. Acad. Sci. USA* 92, 6339–6343; EP 0 655 506) in order to create an enzyme that does not discriminate against ddNTPs. In this set-up Mg is present from the beginning in a range between 0.5 mM and 20 mM, no extra Mn is required. A suitable buffer additionally may comprise but is not limited to Tris-HCl (pH 6.5 to 11), KCl (2 mM–100 mM), and additional enzymes, such as thermostable pyrophosphatase (0,1–50 U). In addition, at least one nucleotide must be present. The reactions are cycled as disclosed above. The enzyme thus can contain activities to perform the reactions of reverse transcription, amplification and sequencing.

This methodology which includes a controlled release of various enzymes from inhibition and thereby adding their activities sequentially or simultaneously to an ongoing reaction without opening the tube or vessel can be applied to numerous combinations of enzymes. A further example is the simultaneous amplification and sequencing of RNA. Here, the reverse transcriptase carrying enzyme may be active from the start, whereas additional enzymes for amplification sequencing remain inactive until released. Thus, reverse transcription may occur without potentially inhibiting effect of other enzymes. One may also envision the combination of an amplification enzyme and a DNA modifying enzyme. Here, the first could amplify the target which is subsequently modified after the release of the second enzyme.

Therefore is one embodiment of the present invention the inventive method wherein the said nucleic acid molecule is RNA, and one of the two polymerases exhibits reverse transcriptase activity. In another preferred embodiment an additional enzyme is present exhibiting reverse transcriptase activity.

Sequential hot-start sequencing ladders are shown in FIG. 3. Both processes, amplification and sequencing, are performing with high efficiency and therefore earlier production of a sequencing ladder can be observed and the accuracy is improved.

An especially preferred embodiment of this invention is the use of more than one primer pair or the use of a second primer pair (FIG. 6) called "silent primer". Therefore, one embodiment according to the present invention is a method for sequencing a nucleic acid molecule in a thermocycling reaction which initially comprises a nucleic acid molecule, a primer pair which comprises a first primer (i) and a second primer (ii) wherein the 3' end of the first primer (i) and the 3' end of the second primer (ii) face each other when annealed on their template, and at least one primer, the first primer (i) or the second primer (ii) is labeled, a reaction buffer, deoxynucleotides, or derivatives thereof, and at least one dideoxynucleotide or another terminating nucleotide (in case of a sequencing reaction), a thermally stable DNA polymerase in the buffer or under conditions that are used for thermal cycling, characterized in that the reaction further comprises at least one further primer (iii) which is either unlabeled or labeled in a different way from the label attached to either primers (i) and/or (ii) and located at or outside the region encompassed by the primers (i) and (ii). The reaction may contain additionally a second enzyme as e.g. a DNA polymerase.

The following combinations of primers could be used in a further preferred embodiment of the method of the invention (see FIG. 6).

In case A, FIG. 6 wherein one primer pair is used in a "Sequential DEXTAQ" reaction, both primers could be differently labeled or one of the two primers could be labeled.

In case B, FIG. 6 wherein more than one primer pair is used, two primers are not labeled and located on opposite strands of the template and an additional primer is labeled, when the unlabeled primers are flanking primers to the labeled primer, which can be fully or partially overlapping or not overlapping to one of the two primers.

In case C, FIG. 6 wherein two primer pairs are used, one primer pair, spanning the region to be sequenced are labeled and an additional primer pair is not labeled, when the unlabeled primers are flanking primers to the labeled primers, which can be fully or partially overlapping or not overlapping to each of the two primers.

In case D, FIG. 6 a special embodiment of case C with partially overlapping primers is shown, when the labeled primers bind to flanking primers at that part of the primer sequence that is created after the first cycle and does not match to the template to be sequenced.

In case E, FIG. 6 another special embodiment is shown, when a label of a primer is not the only one label, but a collection of four different labels, more specified each label for a different nucleotide. Moreover it is preferable that when more than one primer pair is used, the annealing conditions of the flanking primers are different from the labeled primers.

The "silent primer" (primer (iii) and eventually (iv)) serve for the production of DNA fragments which are not or different labeled and are taken as template molecules in the later cycles for the sequencing part of the reaction. The use of a second "silent" primer pair produces higher amounts of nucleic acid fragments serving as templates for the sequencing reaction, which are composed of DNA strands produced by elongation of the silent primers during the amplification cycles and DNA strands produced by elongation of the labeled or biotinylated primers. The use of the silent primers at a large excess compared to the labeled or biotinylated primers leads to a higher amount of template molecules for the sequencing reaction, produced by elongation of the silent primers. Variation of this method are encompassed by the present invention as the use of primers having different annealing properties.

Accordingly, subject of the present invention is also a method for sequencing a nucleic acid molecule in a thermocycling reaction which initially comprises a nucleic acid molecule, a first primer pair which comprises a first primer and a second primer, a reaction buffer, deoxynucleotides or derivatives thereof and at least one dideoxynucleotide or another terminating nucleotide, a thermostable DNA polymerase having a reduced discrimination against ddNTPs compared to wild-type Taq DNA polymerase in the buffer or under the conditions that are used for the thermocycling, and further comprising a second primer pair (primer (iii) and eventually (iv)) called "silent primers", which are not or differently labeled.

Moreover all above described sequential methods for sequencing a nucleic acid molecule in a thermocycling reaction may further comprise a second primer pair called "silent primers" which comprises a third and eventually a forth primer, which are not labeled or differently the labeled as the first primer pairs.

Most preferred embodiment of the present invention is the combination of sequential DEXTAQ with the "silent primer" method.

The relative signal intensity was evaluated by dividing the integral of the primer peak and the integral of the signal peak. The value of the ratio is smaller, when the signal strength is higher and the peaks are more distinct resulting in a more accurate base calling. FIG. 5 shows a comparison of sequential DEXTAQ and sequential DEXTAQ with silent primers concerning the ratio of signal peak areas to the primer peak areas which is in case of sequential DEXTAQ 0,04 and in case of sequential DEXTAQ with silent primer 0.006. The reaction according to the experiment as shown in FIG. 5 was performed according to Example 3. The ratios shown were processed by the fragment manager 1.1 (Amersham Pharmacia Biotech, Uppsala, Sweden). The integral values are relative and not absolute values and therefore have to be considered in relation of two values, like the ratio of the integral of an average signal to the primer signal. The integration of the area under one peak is a measurement of the fluorescence signal and therefore related to the amount of labeled DNA fragments of a distinct size. Nevertheless, the value of the integral has to be smaller if there is less background signal, minute truncation of the DNA fragments of one size and no superposition with neighbored signals. The ratio of the integral of the average signal peaks and the primer peak is a measurement of the quality of the sequence data that is high signal strength and accurate peaks resulting in low values of this ratio. The ratio of the Sequential DEXTAQ reaction is about 0.04 and the value of the same ratio of the Sequential DEXTAQ reaction when using additional silent primers is much lower, 0.006. The difference in this value of one decimal power is caused by more minute truncation of the fragments, less background signals and related to the primers a higher signal strength. This is the reason for having more template molecules in the reaction, which allows to use less labeled Primer and to generate more truncated fragment leading to signals of higher strength. The reduction of the labeled primer precedes in the line DEXTAQ, Sequential DEXTAQ, because of the separated amplification and template generation and a even higher reduction when silent primers are used additionally in Sequential DEXTAQ.

Suitable sources of nucleic acid molecules in the method according to the invention are body fluids such as sperm, urine, blood or fractions of these, hairs, an individual cell, cells or fractions thereof, hard tissue such as bones and soft tissue or fractions thereof and cell cultures or fractions thereof as well as bacteria, viruses or bacteriophages.

The present invention also provides for an application of the method according to the invention for the determination of a nucleotide sequence of a given nucleic acid molecule e.g. for sequencing Shotgun libraries using two labels for large-scale genome projects and in medical diagnostics, forensics and population genetics. The method of the present invention can be used to detect genetic mutations or polymorphisms, to identify the origin of the sequenced nucleic acid or to detect the presence of foreign or infectious agents in a sample.

A particular advantage of the method according to the invention is therefore the ability to directly sequence nucleic acids. Thus the method according to the invention can be used for the direct sequencing of e.g. eukaryotic genomic DNA such as e.g. of human, chromosomal DNA or mitochondrial DNA, human RNA, unpurified plasmid DNA from bacterial colonies as well as unpurified single-stranded or double-stranded DNA from bacteriophages.

The present invention relates to all combinations of all procedures of the above methods.

After preparation the sequencing reactions can be applied directly to a sequencing gel such as e.g. after addition of a commonly used loading buffer (e.g. formamide which contains 20 mM EDTA (pH 7.4) and 6 mg/ml dextran blue) and denaturation (e.g. for 4 minutes at 96° C.). The sequence ladder can be read in correspondence with known methods. The method of the invention is well suited for automation. Since at least one primer in the reaction is labeled, two primers are differently labeled, or the truncated fragments are labeled differently at the 3'-end which can for example be detected with at least two different wavelengths, the method of the present invention enables the simultaneous sequencing of both strands of a template and the detection of both reactions in one or several lanes. In general many sequential DEXTAQ reactions using different dyes can be carried out simultaneously in the same tube and applied to a sequencing instrument that is equipped with several lasers or can be detected by other methods such as e.g. autoradiography.

Subject of the present invention is a kit for synthesizing a nucleic acid molecule containing a first primer (i), a second primer (ii), a reaction buffer, deoxynucleotides or derivatives thereof wherein the thermocycling reaction contains at least two thermostable enzymes with different enzyme activities, whereas at least one enzyme exhibits DNA polymerase activity wherein one of the two enzymes is activated in a later cycle of the thermocycling reaction than the other thermostable enzyme. Kit for sequencing a nucleic acid molecule containing the components as claimed in claim 32 containing a first and a second thermostable DNA polymerase which, in comparison to the said first thermostable DNA polymerase, has a reduced ability to incorporate dideoxynucleotides, and additionally at least one dideoxynucleotide or another terminating nucleotide.

Especially preferred is a kit for sequencing a nucleic acid molecule wherein both polymerases are initially inhibited by inhibiting agents or by chemical modifications and can be activated in later cycles of the thermocycling sequencing reaction wherein one of the polymerases is activated in a later cycle than the other. Especially preferred is the kit according to the present invention whereas the first DNA polymerase is initially inhibited by an inhibiting agent and whereas the second polymerase is initially inhibited by an antibody whereas the second polymerase is released in earlier cycles that the first polymerase.

A further subject of the present invention is a kit for sequencing a nucleic acid molecule containing a first primer, a second primer, a reaction buffer, deoxynucleotides or derivatives thereof and at least one dideoxynucleotide or another terminating nucleotide a thermostable DNA polymerase having a reduced discrimination against ddNTPs compared to wild-type Taq DNA polymerase in the buffer or under the conditions that are used for the thermocycling, and further comprising one or more primers, which are characterized as seen in FIG. 6. In a preferred embodiment of this kit a second DNA polymerase which has a reduced ability to incorporate dideoxynucleotides in comparison to the first thermostable DNA polymerase is comprised.

An especially preferred kit are the above described kits for sequencing a nucleic acid molecule further comprising a second primer pair called "silent primers" which comprises a third and a forth primer, which are not or differently labeled, compared to the first primer pair which is labeled or biotinylated.

A preferred embodiment is a kit for sequencing a nucleic acid molecule as claimed in claim 32–34 containing further at least one further primer (iii) which is unlabeled or labeled in a different way from the label attached to either primer (i) and/or (ii) and located at or outside the region encompassed by the primers (i) and (ii). Kit for sequencing a nucleic acid molecule according to claim 35 comprising further a fourth primer (iv) wherein the 3' end of the primer (iii) and the 3' end of the primer (iv) face each other when amealed on their template and wherein primer (iv) is unlabeled or labeled in different way from the label attached to either primers (i) and/or (ii) and located at or outside the region encompassed by the primers (i) and (ii).

The teaching of the applications EP 0 849 364 and EP 0 854 196, especially examples and figures, is enclosed herein as reference.

BRIEF DESCRIPTION OF THE DRAWINGS

FIGS. 2a–2c. Schematic representation of non-complex, medium complex and complex mixtures which can be sequenced according to the present invention FIGS. 3A and 3B. The comparison of the DEXTAQ (FIG. 3A) and the sequential DEXTAQ method clearly shows that the production of higher amounts of template molecules by separating the processes of amplification and sequencing (FIG. 3B) leads to an earlier production of truncated and labeled DNA fragments, cycle number 20 in case of the sequential DEXTAQ method compared to cycle number 30 in case of the DEXTAQ method, and therefore to a sequencing ladder of higher accuracy, which is documented in a higher reading length (400 compared to 378) and less ambiguities (2 compared to 11).

The invention is described more exactly and in more detail by the following non-limiting examples.

EXAMPLE 1

Figure 1:
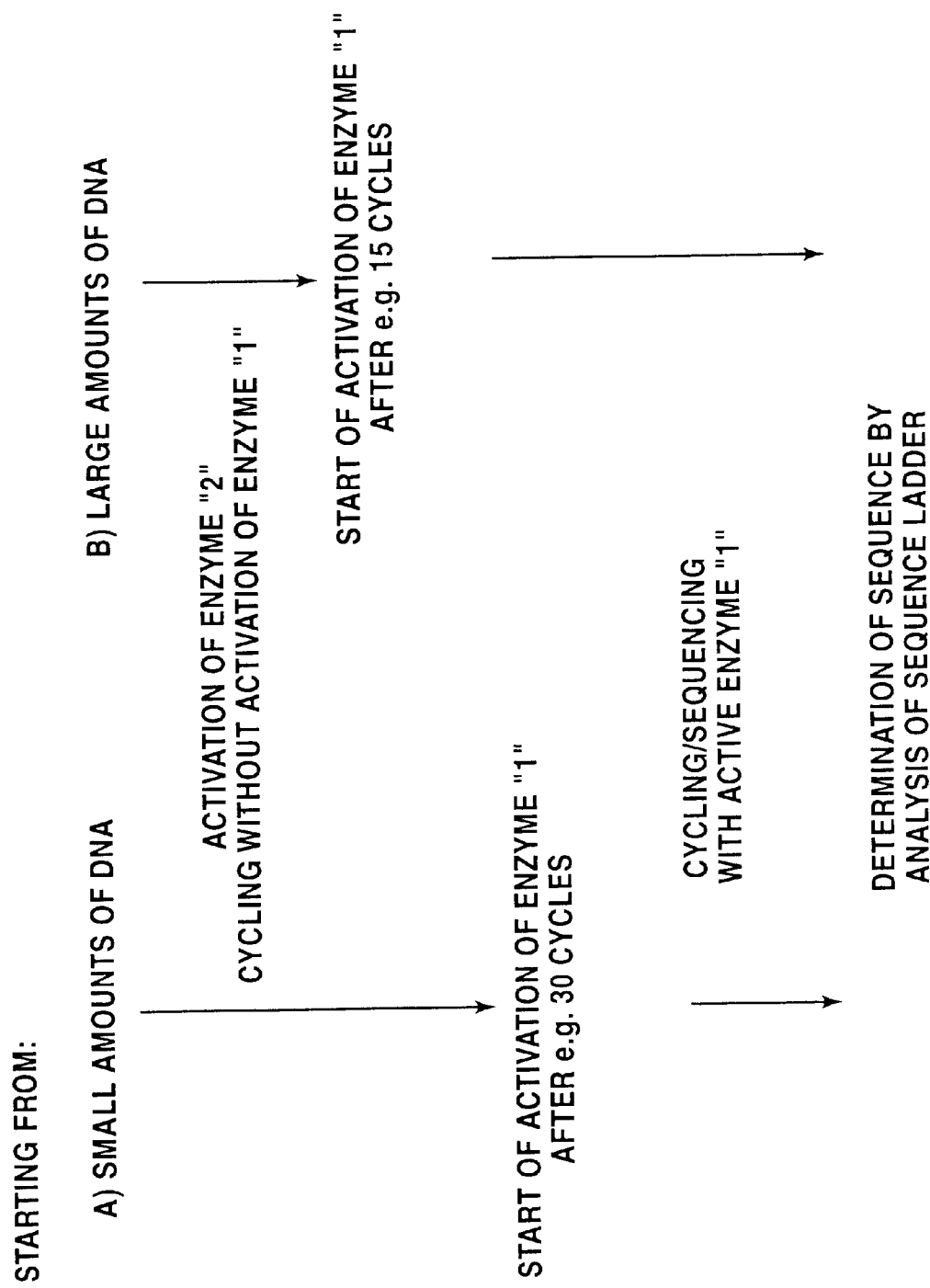
FIG. 1. Schematic representation of two experiments, one in which small amounts of DNA (A) are used as substrate and one in which more substrate DNA is present (B). By activating the second enzyme only after the amplification phase, this amplification phase can be performed for several cycles without the influence of a further enzyme thus e.g. for more cycles when starting from little DNA (A) and fewer cycles (B) when starting from much DNA.
Figure 3A:
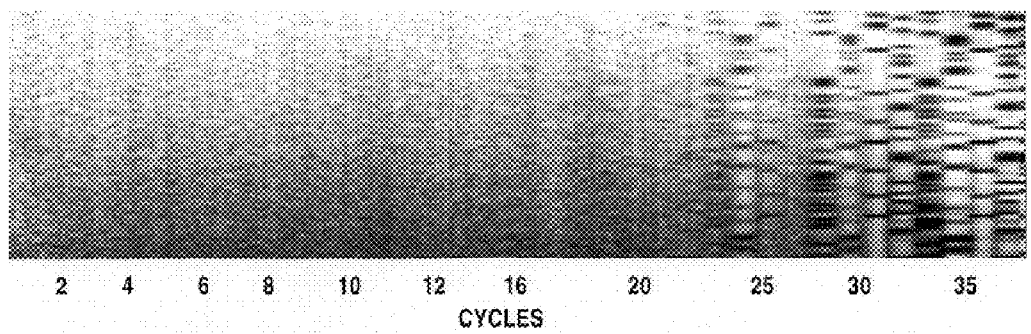
Figure 3B:
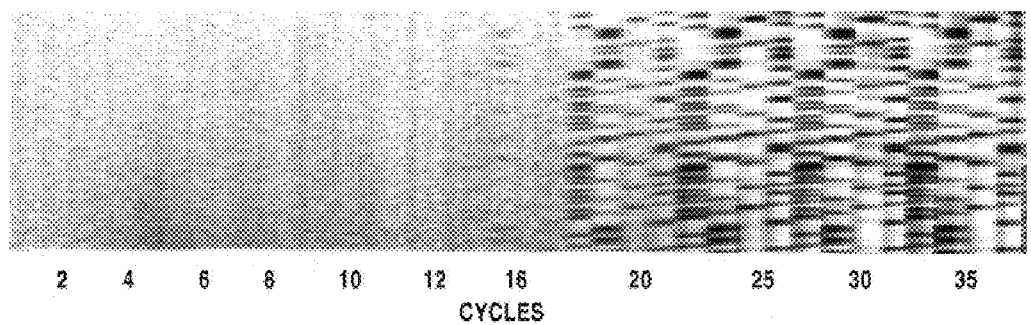
Figure 4A:
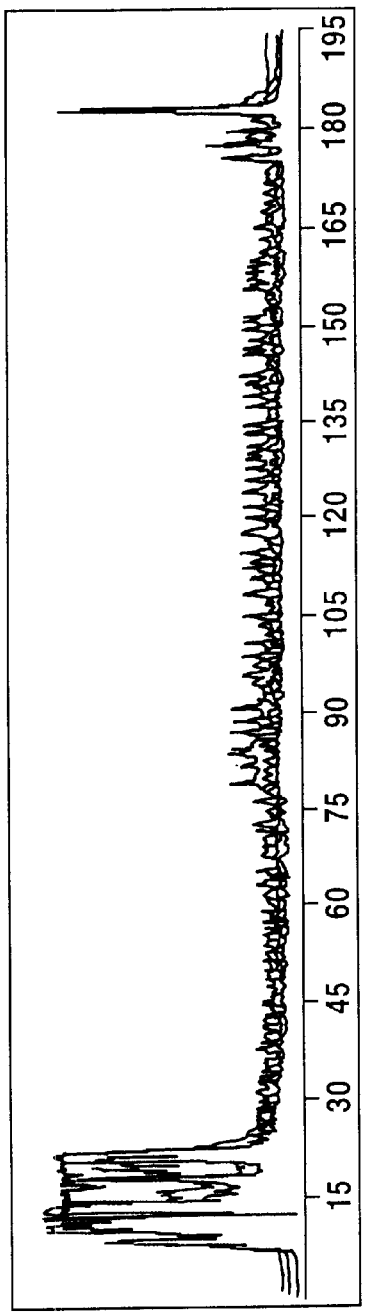
FIGS. 4A and 4B. comparison of sequential DEXTAQ reactions, performed with one labeled primer pair and in the second case performed with addition of a second "silent" primer pair. The comparison of the reading length shows that with the silent primer method 461 bases of the 469 bases spanning DNA region could be read with 1.5% ambiguities, whereas 29 bases less could be read with the one primer pair method at 0.4% ambiguities.
Figure 4B:
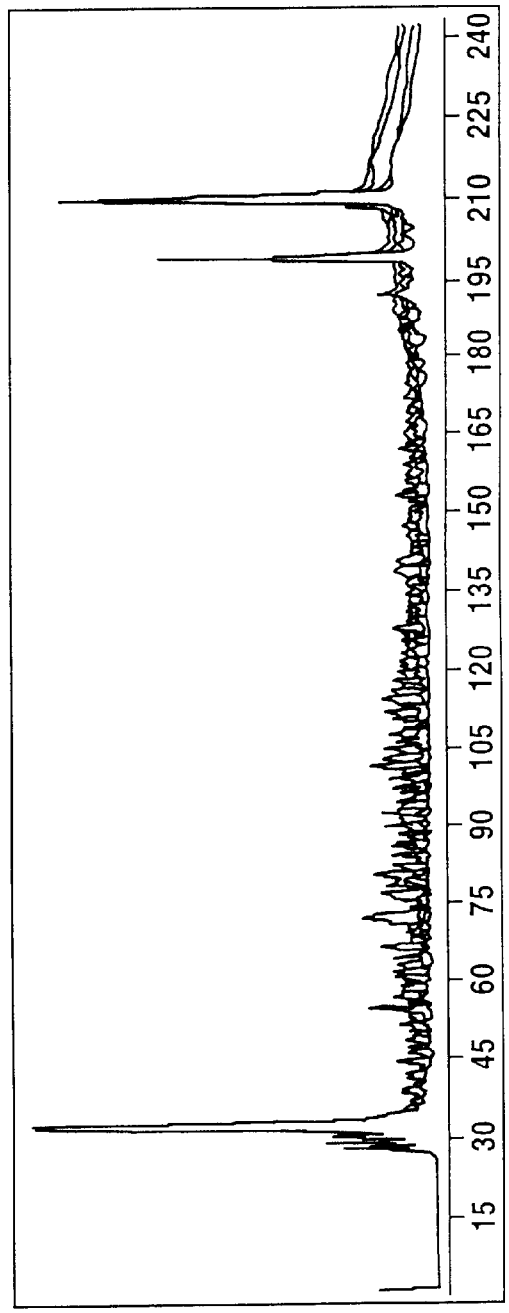

200 ng human genomic DNA (Roche Molecular Biochemicals, Mannheim, Germany) was subjected to a uncoupled direct exponential and amplification and sequencing reaction using 6 pmol of a IRD 700 labeled Primer mtDNA1(5'-GATTCTAATTTAAACTATTCTCTGTTC-3'; SEQ ID NO: 1) and a IRD 800 labeled primer mtDNA2(5'-TTATGACCCTGAAGTAGGAACCAGATG-3'; SEQ ID NO: 2) synthesized by MWG-biotech AG Munich, Germany). The Primers span a region of 469 base pairs (without counting the primer length) of the human mitochondrial control region. The reactions were carried out using 2.5 U Taq DNA polymerase (Roche Molecular Biochemicals, Mannheim, Germany), about 0.5 U of Pyrophosphatase (Roche Molecular Biochemicals, Mannheim, Germany), and about 9 U of AmpliTaq® FS DNA polymerase (Perkin Elmer Corporation, Foster City, Calif., USA) (FIG. 3A) and 9 U of AmpliTaq® FS DNA polymerase (Perkin Elmer Corporation, Foster City, Calif., USA) modified chemically with a polymerase-inhibiting agent (FIG. 3A). The gel picture in FIG. 3 A shows the reaction stopped at different cycles: 2, 4, 6, 8, 10, 12, 16, 20, 25, 30, 35. The cycle sequencing reactions were run in a Primus 96 Cycler (MWG-biotech AG, Munich, Germany) under the following cycling conditions applying an incubation step of 5 min at 95° C. followed by 30 cycles of 40 s at 95° C. (denaturing), 20 s at 62° C. (annealing) and 60 s at 72° C. (synthesis). The A.L.F. software was able to process 378 bases with 11 ambiguities for the IRD 700 labeled primer. The gel picture in FIG. 3B shows the reaction stopped at different cycles: 2, 4, 6, 8, 10, 12, 15, 20, 25, 30, 35. The cycle sequencing reaction was performed as follows: 15 cycles of 95° C. 20s, 62° C. 20s, 68° C. 60s then 95° C. 7 min then 35 cycles of 95° C. 40s, 62° C. 20s, 70° C. 60s. At 95° C. 7 min. is the releasing step of the DNA polymerase "1" ( EP 0 771 870), which carries the Tabor Richardson mutation for efficient incorporation of dideoxynucleotides. The Lanetracker software (EMBL, Heidelberg, Germany) was able to process 400 bases with 2 ambiguities for the IRD 700 labeled primer.

EXAMPLE 2

200 ng human genomic DNA (Roche Molecular Biochemicals, Mannheim, Germany) was subjected to a uncoupled direct exponential and amplification and sequencing reaction using 6 pmol of a IRD 700 labeled Primer mtDNA1 and a IRD 800 labeled Primer mtDNA2 (synthesized by MWG-biotech AG Munich, Germany). The Primers span a region of 469 base pairs (without counting the primer length) of the human mitochondrial control region. The reactions ware carried out using 2,5 U Taq DNA polymerase (Roche Molecular Biochemicals, Mannheim, Germany), about 0,5 U of Pyrophosphatase (Roche Molecular Biochemicals, Mannheim, Germany) and about 9 U of AmpliTaq® FS DNA polymerase (Perkin Elmer Corporation, Foster City, Calif., USA) (FIG. 3A) and 9 U of AmpliTaq® FS DNA polymerase (Perkin Elmer Corporation, Foster City, Calif., USA) modified chemically with a polymerase-inhibiting agent (FIG. 3A). The cycle sequencing reactions were performed in a Primus 96 Cycler (MWG-biotech AG, Munich, Germany) under the following cycling conditions applying an incubation step of 5 min at 95° C. followed by 30 cycles of 40 s at 95° C. (denaturing), 20 s at 62° C. (annealing) a 72° C. (synthesis) is the releasing step of the DNA polymerase "1", ( EP 0 771 870), which carries the Tabor Richardson mutation for efficient incorporation of dideoxynucleotides. The A.L.F. software was able to process 432 bases with 2 ambiguities for the IRD 700 labeled primer in case of the sequential DEXTAQ method with one primer pair and 432 bases with 7 ambiguities in case of the sequential DEXTAQ method with two primer pairs, one labeled and one unlabeled pair. The nucleotides were used at a ratio of 1/200 ddNTP/dNTP, at a concentration of 1 mM of each dNTP.

EXAMPLE 3

200 ng human genomic DNA (Roche Molecular Biochemicals, Mannheim, Germany) was subjected to a uncoupled direct exponential and amplification and sequencing reaction using 2 pmol of a IRD 700 labeled Primer p53 13011fw62 and a IRD 800 labeled Primer p53 13563rev62 (synthesized by MWG-biotech AG Munich, Germany) and in case of the silent primer variant additional 15 pmol of unlabeled Primers were used ( p53 12958fw57 and p53 13592rev57). The Primers span a region of 580 (FIG. 5, part A2 and B2) and in the second case the primers p53 13972fw60 and p53 14902rev59 span a region of 510 base pairs (FIG. 5, part A1 and B1), without counting the primer length of the p 53 gene. The reactions ware carried out using 2 U Taq DNA polymerase (Roche Molecular Biochemicals, Mannheim, Germany), about 0,5 U of Pyrophosphatase (Roche Molecular Biochemicals, Mannheim, Germany) and about 20 U of AmpliTaq® FS DNA polymerase (Perkin Elmer Corporation, Foster City, Calif., USA) (FIG. 3A) and 20 U of AmpliTaq® FS DNA polymerase (Perkin Elmer Corporation, Foster City, Calif., USA) modified chemically with a polymerase-inhibiting agent.

Primer sequences:

P53 13011fw62: 5'-CTTGTGCCCTGACTTTCAACTCT (SEQ ID NO: 3), labeled;

P53 13563rev62: 5'-CTTTGCACATCTCATGGGGTTAT (SEQ ID NO: 4), labeled;

P53 12958fw57: 5'-GCTTACACATGTTTGTTTCTTTG (SEQ ID NO: 5), not labeled;

P53 13592rev57: 5'-TTCAACTGTGCAATAGTTAAACCC (SEQ ID NO: 6), not labeled;

P53 13972fw60: 5'-CTCATCTTGGGCCTGTGTTATC (SEQ ID NO: 7), labeled;

P52 14902rev59: 5'-TGGTATAAGTTGGTGTTCTGAAGTTAG (SEQ ID NO: 8), labeled.

Figure 5A:
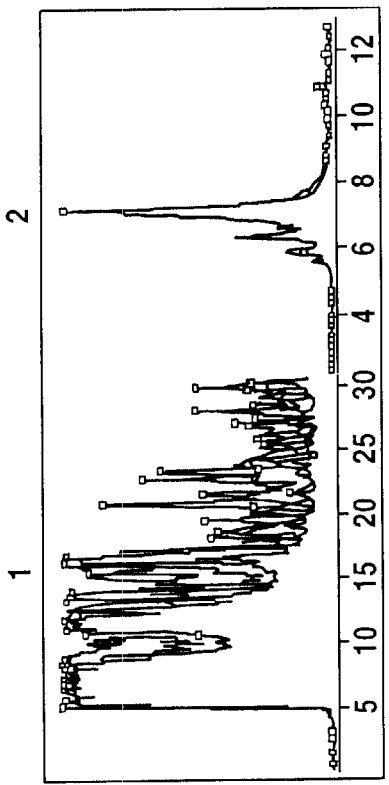
FIG. 5. Comparison of the ratio signal to primer peak 1) sequential DEXTAQ 2) sequential DEXTAQ (silent primer).
Figure 5B:
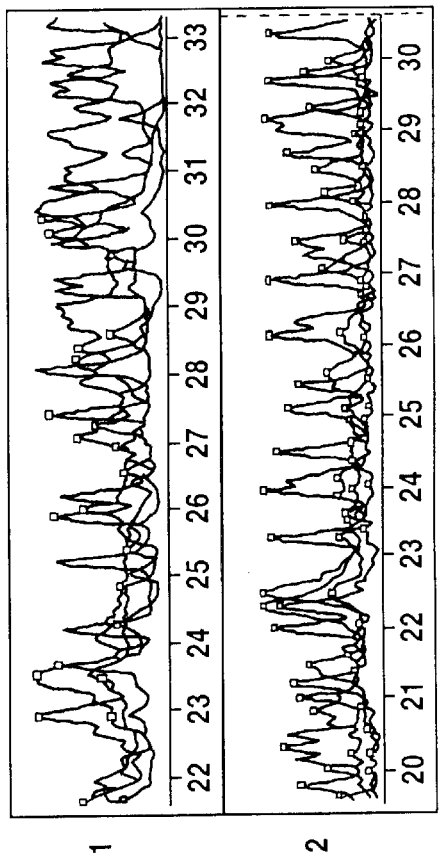
Figure 6A:
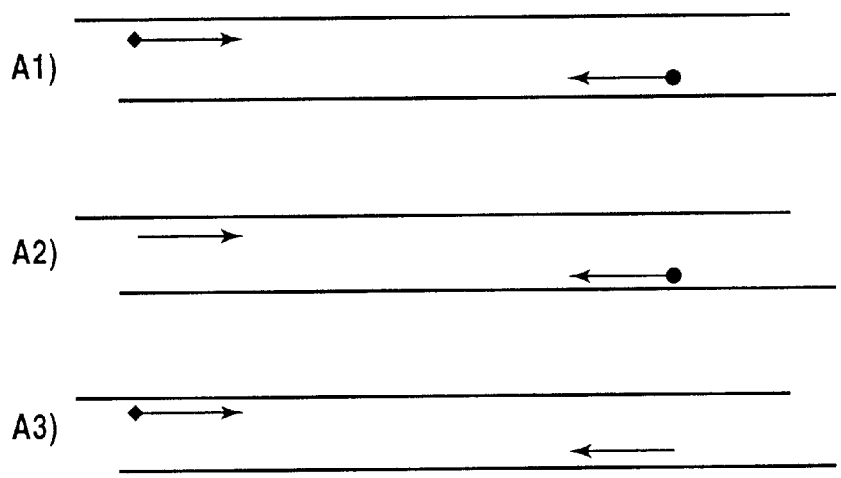
FIG. 6. Silent primer method (A–E).
Figure 6B:
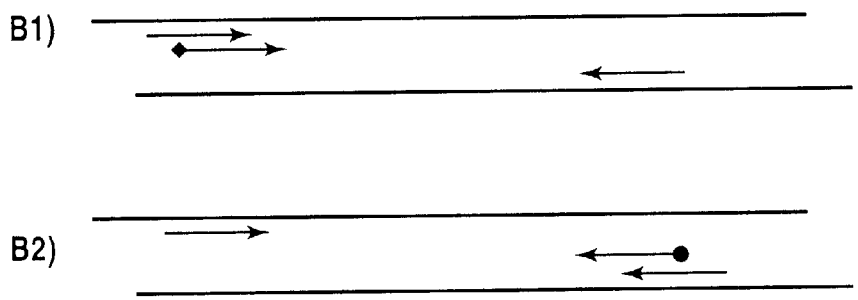
Figure 6C:
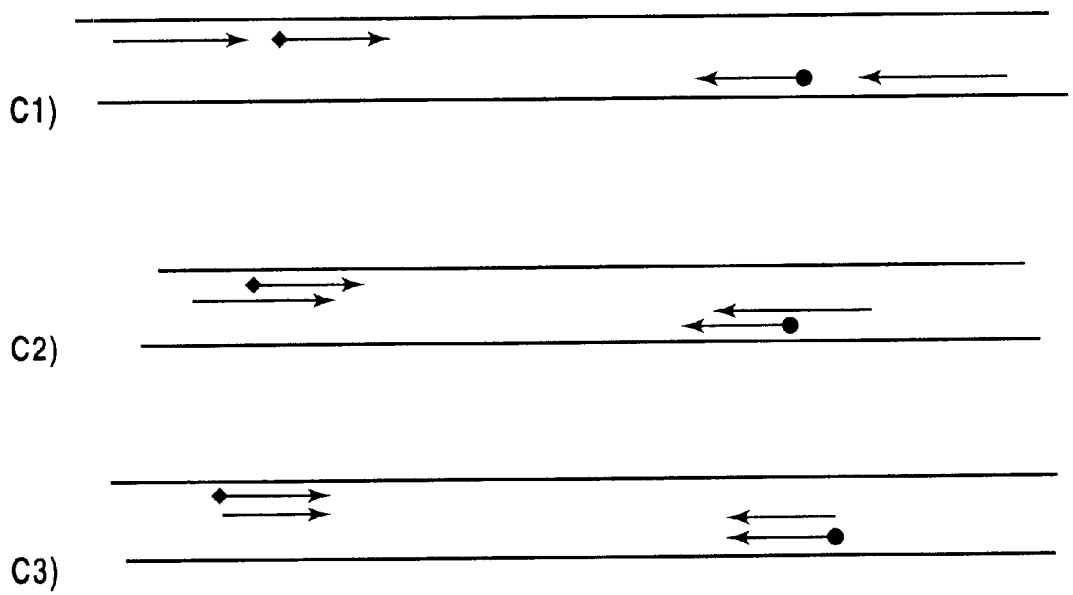
Figure 6D:
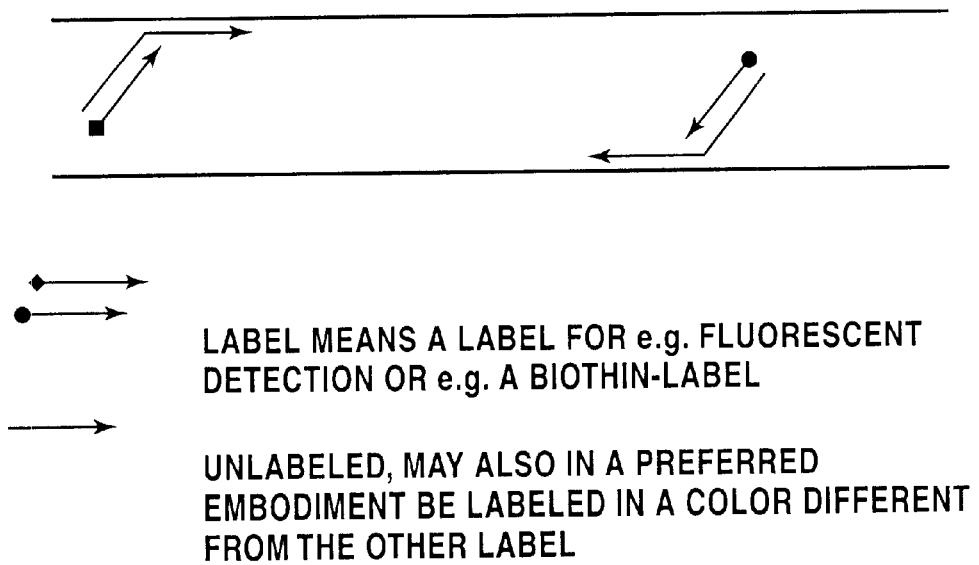
Figure 6E:
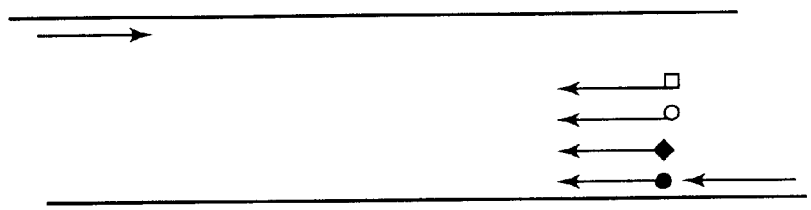
Figure 6F:
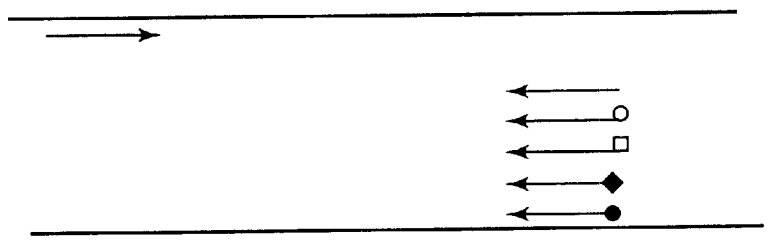

The cycle sequencing reaction were run in a Primus 96 Cycler (MWG-biotech AG, Munich, Germany) under the following cycling conditions applying initial 15 cycling steps of 40 s at 95° C. (denaturing), 20 s at 60° C. (annealing) and 60 s at 72° C. (synthesis) followed by an incubation step of 10 min at 95° C. followed by 30 cycles of 40 s at 95° C. (denaturing), 20 s at 62° C. (annealing) and 60 s at 72° C. (synthesis). The incubation step is the releasing step of the DNA polymerase"1", (EP 0771 870), which carries the Tabor Richardson mutation for efficient incorporation of dideoxynucleotides. The analysis of the readable sequence was processed by the fragment manager 1.1 (Amersham Pharmacia Biotech, Uppsala, Sweden) and is shown in FIG. 5. The nucleotides were used at a ratio of 1/200 ddNTP/dNTP, at a concentration of 1 mM of each dNTP.

What is claimed is:

1. A method for sequencing nucleic acid in a reaction mixture of a thermocycling reaction wherein the reaction mixture contains at least one nucleic acid molecule and at least one dideoxynucleotide or other terminating nucleotide, said method comprising (1) providing in the thermocycling reaction mixture a first primer (i), a second primer (ii), a reaction buffer, at least one deoxynucleotide or derivative thereof, and at least two thermostable DNA polymerases with different enzyme activities for incorporating dideoxynucleotides; and (2) activating through elevated temperature at least one of the thermostable DNA polymerases in a later cycle of the thermocycling reaction than another thermostable DNA polymerase.

2. The method for sequencing a nucleic acid molecule as claimed in claim 1, said method comprising providing in the thermocycling reaction mixture the at least two thermostable DNA polymerases which comprise a first thermostable DNA polymerase and a second thermostable DNA polymerase which has a reduced ability to incorporate dideoxynucleotides in comparison to the first thermostable DNA polymerase.

3. The method for sequencing a nucleic acid molecule as claimed in claim 2, said method comprising activating the first thermostable DNA polymerase in the later cycle of the thermocycling reaction as compared to the second thermostable DNA polymerase having the reduced ability to incorporate dideoxynucleotides in comparison to the first thermostable DNA polymerase.

4. The method for sequencing a nucleic acid molecule as claimed in claim 1, said method comprising initially inhibiting at least one of the thermostable DNA polymerases with a polymerase inhibiting agent so that the initially inhibited DNA polymerase activates in a later cycle of the thermocycling reaction than the other thermostable DNA polymerase.

5. The method for sequencing a nucleic acid molecule as claimed in claim 1, said method comprising chemically modifying the later activated thermostable DNA polymerase so that the initially inhibited thermostable DNA polymerase can be activated in a later cycle of the thermocycling reaction than the other thermostable DNA polymerase.

6. The method for sequencing a nucleic acid molecule as claimed in claim 1, said method comprising initially inhibiting the first and second thermostable DNA polymerases by inhibiting agents or by chemical modifications and activating the first and second thermostable DNA polymerases in later cycles wherein one of the polymerases is activated in a later cycle than the other.

7. The method for sequencing a nucleic acid molecule as claimed in claim 6, said method comprising activating the first thermostable DNA polymerase in a later cycle of the thermocycling reaction than the second thermostable DNA polymerase which has a reduced ability to incorporate dideoxynucleotides in comparison to the first thermostable DNA polymerase.

8. The method for sequencing a nucleic acid molecule as claimed in claim 1, wherein the first thermostable DNA polymerase has a reduced discrimination against ddNTPs compared to wild-type Taq DNA polymerase in the buffer or under the conditions of thermocycling.

9. The method for sequencing a nucleic acid molecule as claimed in claim 1, wherein the first thermostable DNA polymerase is a DNA Taq polymerase (-exo5'-3')(F667Y) or a functional derivative thereof.

10. The method for sequencing a nucleic acid molecule as claimed in claim 1, wherein the second thermostable DNA polymerase is Taq polymerase or a functional derivative thereof.

11. The method for sequencing a nucleic acid molecule as claimed in claim 1, wherein the ratio of said primers is not equal to 1.

12. The method for sequencing a nucleic acid molecule as claimed in claim 1, wherein said method is carried out in one step and in a single container, vessel or tube.

13. The method for sequencing a nucleic acid molecule as claimed in claim 1, said method including the step of labeling the first primer.

14. The method for sequencing a nucleic acid molecule as claimed in claim 1, said method including the step of labeling differently the first and second primer.

15. The method for sequencing a nucleic acid molecule as claimed in claim 1, said method including the step of labeling at least one ddNTP or other terminating nucleotide.

16. The method for sequencing a nucleic acid molecule as claimed in claim 1, said method comprising providing in the reaction mixture a thermostable pyrophosphatase.

17. The method as claimed in claim 1, wherein the nucleic acid molecule is genomic DNA.

18. The method as claimed in claim 1, wherein the nucleic acid molecule is RNA, and one of the two thermostable DNA polymerases exhibits reverse transcriptase activity.

19. The method as claimed in claim 1, said method comprising providing in the reaction mixture an enzyme exhibiting reverse transcriptase activity, and wherein the nucleic acid molecule is RNA.

20. The method as claimed in claim 1, said method comprising providing in the reaction mixture at least one third primer (iii) which is unlabeled or labeled in a different way from a label attached to either primer (i) and/or (ii) and located at or outside the region encompassed by the primers (i) and (ii).

21. The method according to claim 20, said method comprising providing in the reaction mixture a fourth primer (iv) wherein the 3' end of the primer (iii) and the 3' end of the primer (iv) face each other when annealed on their template and wherein primer (iv) is unlabeled or labeled in different way from the label attached to either primers (i) and/or (ii) and located at or outside the region encompassed by the primers (i) and (ii).

22. The method according to claim 1, wherein the nucleic acid molecule that is sequenced is eukaryotic genomic DNA.

23. The method according to claim 1, wherein the nucleic acid molecule that is sequenced is human chromosomal or mitochondrial DNA.

24. The method according to claim 1, wherein the nucleic acid molecule that is sequenced is human RNA.

25. The method according to claim 1, further comprising directly sequencing the nucleic acid molecule which is unpurified plasmid DNA from bacterial colonies.

26. The method according to claim 1, further comprising directly sequencing the nucleic acid molecule which is unpurified single-stranded or double-stranded DNA from bacteriophages.

27. A method for detecting genetic mutations or polymorphisms, comprising (1) sequencing nucleic acid by the method according to claim 1, and (2) identifying at least one genetic mutation or polymorphism in the sequenced nucleic acid molecule.

28. A method for identifying the origin of nucleic acid, comprising (1) sequencing nucleic acid by the method according to claim 1, and (2) identifying the origin of the sequenced nucleic acid molecule.

29. A method for detecting the presence of foreign or infectious agents in a sample, comprising (1) providing in a reaction mixture the sample that contains the nucleic acid molecule that derives from a foreign or infectious agent, (2) sequencing the nucleic acid by the method according to claim 1, and (3) identifying the sequenced nucleic acid molecule as being derived from the foreign or infectious agent.

30. A method according to claim 1, wherein the nucleic acid molecule that is sequenced is from a body fluid including sperm, urine, blood or blood samples, hairs, single cells or fractions thereof, tissues or fractions thereof, cell cultures, bacteria, viruses or bacteriophages.

31. A kit for sequencing a nucleic acid molecule in a reaction mixture of a thermocycling reaction, said kit comprising

- a first primer (i),
- a second primer (ii),
- a reaction buffer,
- at least one deoxynucleotide or derivative thereof,
- at least two thermostable DNA polymerases comprising a first thermostable DNA polymerase and a second thermostable DNA polymerase which has a reduced ability to incorporate dideoxynucleotides as compared to the first thermostable DNA polymerase,
- wherein the first or second thermostable DNA polymerase is activatable through elevated temperature in a later cycle of the thermocycling reaction compared to the other thermostable DNA polymerase,
- at least one dideoxynucleotide or other terminating nucleotide, and
- inhibiting agents having a controlled release on the first and second thermostable DNA polymerases, wherein the first and second thermostable DNA polymerases are initially inhibited by the inhibiting agents in the thermocycling sequencing reaction but activatable in later cycles thereof, wherein one of the polymerases is activatable in a later cycle than the other.

32. The kit for sequencing a nucleic acid molecule as claimed in claim 31, said kit comprising at least one third primer (iii) which is unlabeled or labeled in a different way from a label attached to either primer (i) and/or (ii) and located at or outside the region encompassed by the primers (i) and (ii).

33. The kit for sequencing a nucleic acid molecule according to claim 32, said kit comprising a fourth primer (iv) wherein the 3' end of the primer (iii) and the 3' end of the primer (iv) face each other when annealed on their template and wherein primer (iv) is unlabeled or labeled in different way from the label attached to either primers (i) and/or (ii) and located at or outside the region encompassed by the primers (i) and (ii).

34. The kit for sequencing a nucleic acid molecule according to claim 31, wherein the first thermostable DNA polymerase is modified by an antibody and the second thermostable DNA polymerase is chemically modified by a chemical polymerase-inhibiting agent comprising dicarboxylic acid anhydrases.

35. The kit for sequencing a nucleic acid molecule according to claim 31, wherein the first and second thermostable DNA polymerases are chemically modified so that the first and second thermostable DNA polymerases are initially inhibited but activatable in later cycles of the thermocycling sequencing reaction, wherein one of the polymerases is activatable in a later cycle than the other.

* * * * *

SEQUENCE LISTING

```
<160> NUMBER OF SEQ ID NOS: 8

<210> SEQ ID NO 1
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: IRD 700 labeled primer  mtDNA1

<400> SEQUENCE: 1
gattctaatt taaactattc tctgttc                                          27

<210> SEQ ID NO 2
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: IRD 800 labeled primer  mtDNA2

<400> SEQUENCE: 2
ttatgaccct gaagtaggaa ccagatg                                          27

<210> SEQ ID NO 3
<211> LENGTH: 23
<212> TYPE: DNA
<213> ORGANISM: Artificial Sequence
```

```
<220> FEATURE:
<221> NAME/KEY: misc_feature
<222> LOCATION: (1)..(23)
<223> OTHER INFORMATION: IRD 700 labeled primer  P53 13011fw62

<400> SEQUENCE: 3
cttgtgccct gactttcaac tct                                             23

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: RD 800 labeled primer P53 13563rev62

<400> SEQUENCE: 4
ctttgcacat ctcatggggt tat                                             23

<210> SEQ ID NO 5
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer P53 12958fw57

<400> SEQUENCE: 5
gcttacacat gtttgtttct ttg                                             23

<210> SEQ ID NO 6
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: primer P53 13592rev57

<400> SEQUENCE: 6
ttcaactgtg caatagttaa accc                                            24

<210> SEQ ID NO 7
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: labeled primer P53 139 72fw60

<400> SEQUENCE: 7
ctcatcttgg gcctgtgtta tc                                              22

<210> SEQ ID NO 8
<211> LENGTH: 27
<212> TYPE: DNA
<213> ORGANISM: Artificial Sequence
<220> FEATURE:
<221> NAME/KEY: misc_feature
<222> LOCATION: (1)..(27)
<223> OTHER INFORMATION: labeled primer P53 149 02rev59

<400> SEQUENCE: 8
tggtataagt tggtgttctg aagttag                                         27
```